(12) United States Patent
Potin et al.

(10) Patent No.: US 8,765,693 B2
(45) Date of Patent: Jul. 1, 2014

(54) METHOD OF INHIBITING PREMATURE AGING OF HUMAN SKIN CAUSED BY EXPOSURE TO INFRARED RADIATION

(75) Inventors: Anthony Potin, Hoboken, NJ (US); Christian Oresajo, Nanuet, NY (US); Nannan Chen, Princeton, NJ (US); Donna McCann, Oxford, NJ (US)

(73) Assignee: L'Oreal, Paris (FR)

( * ) Notice: Subject to any disclaimer, the term of this patent is extended or adjusted under 35 U.S.C. 154(b) by 3 days.

(21) Appl. No.: 13/584,117

(22) Filed: Aug. 13, 2012

(65) Prior Publication Data
US 2014/0045777 A1  Feb. 13, 2014

(51) Int. Cl.
*A61K 31/70* (2006.01)
(52) U.S. Cl.
USPC .............................................. 514/25; 514/53
(58) Field of Classification Search
USPC .......................................................... 514/25
See application file for complete search history.

(56) References Cited

U.S. PATENT DOCUMENTS

| | | | |
|---|---|---|---|
| 5,427,771 A | 6/1995 | Grollier et al. | |
| 6,448,232 B1 | 9/2002 | Ehrenkranz | |
| 7,179,841 B2 * | 2/2007 | Zielinski et al. | 514/474 |
| 2007/0225360 A1 * | 9/2007 | Pinnell et al. | 514/456 |

OTHER PUBLICATIONS

Bing-Rong et al, "Protective effect of the Baicalin against DNA damage induced by ultraviolet B irradiation to mouse epidermis", Photodermatology, Photoimmunology & Photomedicine, vol. 24, No. 4, Aug. 2008, pp. 175-182.*
Infrared Radiation-Induced Matrix Metalloproteinase in Human Skin: Implications for Protection; Peter Schroeder, Juergen Lademann, Maxim E. Darvin, Helger Stege, Corinna Marks, Susanne Bruhnke and Jean Krutmann—Journal of Investigative Dermatology (2008) 128, p. 2491-2497.
CTFA Cosmetic Ingredient Handbook, 2nd Edition, p. 502-506—The Cosmetic, Toiletry, and Fragrance Association, 1101 17th Street, N.W. Suite 300, Washington D.C. 20036.

* cited by examiner

*Primary Examiner* — Elli Peselev
(74) *Attorney, Agent, or Firm* — L'Oreal USA

(57) ABSTRACT

A method of inhibiting premature aging of human skin caused by exposure to infrared radiation comprising contacting the skin with a composition containing a therapeutically-effective amount of at least one protective compound chosen from baicalin, phloretin and neohesperidin dihydrochalcone, as well as combinations thereof.

17 Claims, No Drawings

METHOD OF INHIBITING PREMATURE AGING OF HUMAN SKIN CAUSED BY EXPOSURE TO INFRARED RADIATION

FIELD OF THE INVENTION

The present invention is directed to a method of inhibiting premature aging of human skin caused by exposure to infrared radiation. More particularly, the invention relates to the use of certain protective compounds, in therapeutically-effective amounts which, when applied onto human skin, inhibit premature aging thereof caused by infrared radiation exposure.

DISCUSSION OF THE BACKGROUND

The role of ultraviolet radiation in the tanning of the human epidermis, but also in skin ageing, and in particular that of erythemogenic UV-B rays of wavelengths between 280 and 320 nm, which are the main cause of protocarcinogenesis, is known. It has also been demonstrated that UV-A rays, of wavelengths between 320 and 400 nm, which cause tanning of the skin, result in photo-aging of the skin. However, solar radiation reaching the earth's surface also comprises 50% of a not insignificant radiation, namely infrared radiation, of wavelengths between approximately 760 nm and 1 mm.

The incidence of infrared radiation on the human epidermis is hence naturally closely linked to exposure to the sun, but also to various other artificial light sources such as, for example, infra-red lasers and infra red light therapy.

SUMMARY OF THE INVENTION

The present invention relates to a method of inhibiting premature aging of human skin caused by exposure to infrared radiation comprising contacting the skin with a composition containing a therapeutically-effective amount of at least one protective compound chosen from baicalin, phloretin and neohesperidin dihydrochalcone, as well as combinations thereof.

DETAILED DESCRIPTION OF THE INVENTION

Other than in the operating examples, or where otherwise indicated, all numbers expressing quantities of ingredients and/or reaction conditions are to be understood as being modified in all instances by the term "about".

Infrared radiation is known to induce up-regulation of MMP-1, which is the main collagen degrading enzyme present in human skin. Collagen degradation, in turn, is known to play a major role in the premature aging of human skin, causing it to appear aesthetically unattractive. Applicant has surprisingly and unexpectedly discovered that certain compounds, when applied onto human skin, provide a significant inhibitory effect on IR-induced upregulation of MMP-1, thereby protecting human skin from appearing prematurely aged.

Protective Compounds

Suitable protective compounds for inhibiting IR-induced premature aging of human skin include, for example, baicalin, phloretin and neohesperidin dihydrochalcone.

Baicalin, a component of Chinese medicinal herb Huang-chin (*Scutellaria baicalensis*), a polyphenol, is a type of flavonoid.

Baicalin may be employed in an amount of from about 0.001 to about 10%, preferably from about 0.001 to about 5% by weight, and most preferably from about 0.001 to about 1% by weight, based on the total weight of the composition.

Phloretin is the aglucone portion of phlorizin and is a polyphenolic compound. It is split from phlorizin by acid hydrolysis. Alternatively, phloretin can be completely synthesized directly by known processes. Suitable phloretin derivatives include, but are not limited to, dihydrochalcone derivatives, such as those disclosed in U.S. Pat. No. 6,448,232, the entire contents of which is hereby incorporated by reference.

Phloretin may be employed in an amount of from about 0.00001 to about 10%, preferably from about 0.0001 to about 10% by weight, and most preferably from about 0.001 to about 5% by weight, based on the total weight of the composition.

Neohesperidin dihydrochalcone is a glycosidic flavonoid. Flavonoids are a family of natural substances that occur in plants. Several flavonone glycosides are unique to citrus. The starting material for the commercial production of neohesperidin dihydrochalcone is either neohesperidin, which can be extracted from bitter orange (*Citrus aurantium*), or naringin, which is obtained from grapefruit (*Citrus paradisii*).

Neohesperidin dihydrochalcone may be employed in an amount of from about 0.001 to about 10%, preferably from about 0.006 to about 10% by weight, and most preferably from about 0.006 to about 5% by weight, based on the total weight of the composition.

The protective compounds will typically be delivered onto human skin via a cosmetically acceptable vehicle such as, for example, non-aqueous solvents, aqueous solutions, oily solutions. Oil/Water emulsions, Water/Oil emulsions.

Non-Aqueous Organic Solvent

Any non-aqueous organic solvent capable of solubilizing the protective compounds may be employed. Examples of suitable solvents include, but are not limited to, non-aqueous polar organic solvents, and non-aqueous non-polar organic solvents.

Non-aqueous Polar Organic Solvent

A variety of non-aqueous polar organic solvents may be used in the anti-aging composition of the present invention. Examples thereof are as follows.

Polyols

Polyols are suitable non-aqueous polar organic solvents. For purposes of this specification, polyols are defined as compounds which contain three or more hydroxyl groups per molecule. Examples of suitable polyols include glucose glutamate, glycerin, 1,2,6-hexanetriol, methyl gluceth-10, methyl gluceth-20, methyl glucose dioleate, methyl glucose sesquicaprylate/sesquicaprate, methyl glucose sesquicocoate, methyl glucose sesquiisostearate, methyl glucose sesquilaurate, methyl glucose sesquistearate, phytantriol, sorbeth-6, sorbeth-20, sorbeth-30, sorbeth-40, thioglycerin, and mixtures thereof. An especially preferred polyol is glycerin.

Polymeric or Monomeric Ethers

Also suitable as the non-aqueous polar organic solvent are homopolymeric or block copolymeric liquid ethers. Polymeric ethers are preferably formed by polymerization of monomeric alkylene oxides, generally ethylene or propylene oxides. Examples of such polymeric ethers include PEG, PPG, and derivatives thereof.

Other examples of suitable polymeric ethers include polyoxypropylene polyoxyethylene block copolymers. Such compounds are sold under the CTFA name Meroxapol 105, 108, 171, 172, 174, 178, 251, 252, 254, 255, 258, 311, 312, and 314.

Mono- and Dihydric Alcohols

Also suitable for use as the non-aqueous polar organic solvent are mono- and dihydric alcohols of the general formula R(OH), where n is 1 or 2 and R is a substituted or unsubstituted saturated $C_{2-10}$, preferably $C_{1-8}$ alkyl, or a substituted or unsubstituted alicyclic, bicyclic, or aromatic ring, with the substituents selected from halogen, alkoxy, hydroxy, and so on. Examples of suitable alcohols include monohydric alcohols such as ethanol, isopropanol, hexyldecanol, benzyl alcohol, propyl alcohol, and isopropyl alcohol, as well as dihydric alcohols such as hexylene glycol, diethylene glycol, ethylene glycol, propylene glycol, 1,2-butylene glycol, 1,5-pentanediol, triethylene glycol, dipropylene glycol, and mixtures thereof.

Sorbitan Derivatives

Sorbitan derivatives, which are defined as ethers or esters of sorbitan, are also suitable polar solvents. Examples of suitable sorbitan derivatives are the Polysorbates, which are defined as stearate esters of sorbitol and sorbitan anhydrides, such as Polysorbate 20, 21, 40, 60, 61, 65, 80, 81, and 85. Also suitable are fatty esters of hexitol anhydrides derived from sorbitol, such as sorbitan trioleate, sorbitan tristearate, sorbitan sesquistearate, sorbitan stearate, sorbitan palmitate, sorbitan oleate, and mixtures thereof.

Non-aqueous Non-polar Organic Solvents

A variety of non-aqueous non-polar organic solvents can be used in the composition of the invention, if so desired. Examples thereof are as follows.

Silicones

Silicones are suitable non-polar compounds. The silicones may be volatile or non-volatile. The term "volatile" means that the silicone has a measurable vapor pressure, i.e. a vapor pressure of at least 2 mm. of mercury at 20° C. If volatile, the silicone generally will have a viscosity of 0.5 to 25 centistokes at 25° C. Suitable volatile silicones include cyclic silicones, linear silicones, or mixtures thereof.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

The silicone may also be nonvolatile, and in particular water insoluble nonvolatile silicones. The term "nonvolatile" means that the silicone has a vapor pressure of less than 2 mm. of mercury at 20° C. A variety of silicones fits this definition including dimethicone, phenyl trimethicone, diphenyl dimethicone, methicone, hexadecyl methicone, stearoxydimethicone, stearyl dimethicone, cetyl dimethicone, and so on.

Cyclomethicone is a preferred silicone for use in the composition of the invention.

Esters

In addition to the sorbitan esters, other esters are also suitable as the non-aqueous non-polar organic solvent. In general such esters have the formula $R^1CO—OR^2$ wherein $R^1$ and $R^2$ are independently a $C_{1-25}$ straight or branched chain saturated or unsaturated alkyl, alkylcarbonyloxyalkyl, or alkoxycarbonylalkyl, aryl, which may be substituted or unsubstituted with halogen, hydroxyl, alkyl, and the like.

Examples of suitable esters include alkyl acetates, alkyl behenates, alkyl lactates, alkyl benzoates, alkyl octanoates, alkyl salicylates, and in particular $C_{12-15}$ alkyl benzoate. Examples of further esters are set forth on pages 502-506 of the CTFA Cosmetic Ingredient Handbook, Second Edition, 1992, which is hereby incorporated by reference.

Fats and Oils

Fats and oils are also suitable as the non-aqueous non-polar organic solvent. Preferably these materials are liquids or semi-solids at room temperature. They are generally defined as glyceryl esters of fatty acids (triglycerides), as well as the synthetically prepared esters of glycerin and fatty acids. Examples of such materials include oils such as apricot kernel oil, avocado oil, canola oil, olive oil, sesame oil, peanut oil, soybean oil, trilinolenin, trilinolein, trioctanoin, tristearin, triolein, sesame oil, rapeseed oil, sunflower seed oil, and so on.

Fatty Acids

Fatty acids are also suitable as the non-aqueous non-polar organic solvent in the compositions of the invention. Preferably the fatty acids are liquid or semi solid at room temperature. Fatty acids are the carboxylic acids obtained by hydrolysis of animal or vegetable fats and oils. Carboxylic acids having alkyl chains shorter than about seven carbon atoms are not generally considered fatty acids. Fatty acids have the general structure $R^3—COOH$ where $R^3$ is a straight or branched chain saturated or unsaturated $C_{7-65}$ alkyl. Examples of suitable fatty acids include arachidic acid, arachidonic acid, behenic acid, capric acid, caproic acid, caprylic acid, coconut acid, corn acid, cottonseed acid, hydrogenated coconut acid, hydroxystearic acid, lauric acid, linoleic acid, linolenic acid, linseed acid, myristic acid, oleic acid, palmitic acid, palm kernel acid, soy acid, tallow acid, and the like.

Fatty Alcohols

Fatty alcohols may also be used as the non-aqueous non-polar organic solvent. Fatty alcohols are generally made by reducing the fatty acid —COOH group to the hydroxyl function. They generally have the formula $R^4CH_2OH$. Examples of fatty alcohols are behenyl alcohol, $C_{9-11}$ alcohol, $C_{12-13}$ alcohol, $C_{12-15}$ alcohol, $C_{12-16}$ alcohol, caprylic alcohol, cetearyl alcohol, cetyl alcohol, coconut alcohol, decyl alcohol, lauryl alcohol, myristyl alcohol, oleyl alcohol, and the like.

Hydrocarbons

Hydrocarbons are also good non-aqueous non-polar organic solvents in accordance with the invention. Examples of suitable hydrocarbons include $C_{7-60}$ isoparaffins, ethane, heptane, hexane, hydrogenated polyisobutene, isobutane, isododecane, isoeicosane, isohexadecane, isopentane, microcrystalline wax, mineral oil, mineral spirits, paraffin, petrolatum, petroleum distillates, squalene, polyethylene, and mixtures thereof. Preferred hydrocarbons are mineral oil and polyethylene.

Lanolin and Lanolin Derivatives

Also suitable as the non-aqueous non-polar organic solvent are lanolin and derivatives thereof. Examples of such materials include acetylated hydrogenated lanolin, acetylated lanolin alcohol, laneth, lanolin acid, lanolin oil, lanolin alcohol, lanolin wax, and so on.

In the event a water soluble active ingredient such as, for example, ascorbic acid and/or ferulic acid is employed in the composition of the present invention, water will be present in the composition as a co-solvent. The water will be employed in an amount at least sufficient to solubilize the ascorbic acid present in the composition.

Ascorbic acid may be employed in an amount of from about 0.001 to about 25% by weight, preferably from about 0.01 to about 20% by weight, and most preferably from about 0.05 to about 20% by weight, based on the total weight of the composition.

Similarly, ferulic acid may be employed in an amount of from about 0.00004 to about 20% by weight, preferably from about 0.0004 to about 20% by weight, and most preferably from about 0.004 to about 10% by weight, based on the total weight of the composition.

In a preferred embodiment of the present invention, the composition is in the form of a single-phase solution, such as cosmetic serums or aerosols, for example. In another embodiment, the composition is in the form of an emulsion, such as creams or lotions, for example.

Other Ingredients

It may also be desired to include certain other ingredients in the composition of the invention, such as other types of antioxidants, anti-inflammatory compounds, surfactants, waxes, colorants, preservatives, and the like.

Surfactants

Silicone Surfactants

The term "surfactant" is defined, in accordance with the invention, as a compound having at least one hydrophilic moiety and at least one lipophilic moiety. The surfactants may be silicone surfactants (also referred to as organosiloxane emulsifiers) or organic surfactants.

Suitable silicone surfactants used in the compositions of the invention may be liquid or solid at room temperature and are generally a water-in-oil or oil-in-water type surfactants which are preferably nonionic, having an Hydrophile/Lipophile Balance (HLB) of 2 to 18. Preferably the organosiloxane is a nonionic surfactant having an HLB of 2 to 12; such as 2 to 10; such as 4 to 6. The HLB of a nonionic surfactant is the balance between the hydrophilic and lipophilic portions of the surfactant and is calculated according to the following formula:

$$HLB = 20(1 - S/A)$$

where S is the saponification number of the surfactant and A is the acid number of the surfactant.

The silicone surfactant or emulsifier used in the compositions of the invention is a polymer containing a polymeric backbone including repeating siloxy units that may have cyclic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature due to the methyl groups, and confer lipophilicity to the molecule. In addition, longer chain alkyl radicals, hydroxy-polypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer. It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, sulfonates, sulfates, phosphates, or amines.

The term "lipophilic radical" means an organic radical that, when substituted onto the organosiloxane polymer backbone, confers lipophilic properties to the substituted portion of the polymer. Examples of organic radicals which will confer lipophilicity are $C_{1-40}$ straight or branched chain alkyl, fluoro, aryl, aryloxy, $C_{1-40}$ hydrocarbyl acyl, hydroxypolypropyleneoxy, or mixtures thereof. The $C_{1-40}$ alkyl may be non-interrupted, or interrupted by one or more oxygen atoms, a benzene ring, amides, esters, or other functional groups.

Organosiloxane polymers useful in the compositions of the invention include those sold by Goldschmidt under the ABIL™ trademark including ABIL B-9806™, as well as those sold by Rhone-Poulenc under the Alkasil™ tradename. Also, organosiloxane emulsifiers sold by Amerchol under the Amersil™ tradename, including Amersil ME-358™, Amersil DMC-287™ and Amersil DMC-357™ are suitable. Dow Corning surfactants such as Dow Corning 3225C™ Formulation Aid, Dow Corning 190™ Surfactant, Dow Corning 193™ Surfactant, Dow Corning Q2-5200™, and the like are also suitable, In addition, surfactants sold under the tradename Silwet™ by Union Carbide, and surfactants sold by Troy Corporation under the Troysol™ tradename, those sold by Taiwan Surfactant Co. under the tradename Ablusoft™, those sold by Hoechst under the tradename Arkophob™, are also suitable for use in the invention.

Also suitable as surfactants are various organic surfactants such as anionic, nonionic, amphoteric, zwitterionic, or cationic surfactants.

The composition of the present invention may contain at least one surfactant in an amount of from about 0.01 to about 15% by weight, such as from about 0.5 to about 10% by weight, such as from about 1 to about 8% by weight, all weights based on the total weight of the total composition.

Waxes

Suitable waxes have a melting point of from about 35 to about 120° C., include animal waxes, plant waxes, mineral waxes, silicone waxes, synthetic waxes, and petroleum waxes.

The composition of the present invention may contain waxes in an amount of from about 0.1 to about 25% by weight, such as from about 0.5 to about 20% by weight, such as from about 1 to about 15% by weight, all weights based on the total weight of the total composition.

Branched Chain Silicone Resins

It may be desirable to include one or more branched chain silicone resins in the compositions of the invention. Examples of suitable silicone resins include, but are not limited to, siloxy silicate polymers such as those commercially available from GE silicones under the trade name of SR1000™, and silicone esters such as those commercially available from General Electric under the tradenames SF1318™ and SF1312™, and the like.

Sunscreens

The composition of the present invention may also contain a sunscreen. If used, they may be present in an amount of from about 0.001 to about 20% by weight, such as from about 0.01 to about 10% by weight, such as from about 0.05 to about 8% by weight, all weights based on the total weight of the composition.

Preservatives

A variety of preservatives may also be employed in an amount of from about 0.0001 to about 8% by weight, such as from about 0.001 to about 6% by weight, such as from about 0.005 to about 5% by weight, all weights based on the total weight of the composition.

Vitamins

The compositions of the invention may contain vitamins and/or coenzymes. Suitable vitamins include, but are not limited to, the B vitamins such as thiamine, riboflavin, pyridoxin, as well as coenzymes such as thiamine pyrophoshate, flavin adenin dinucleotide, folic acid, pyridoxal phosphate, tetrahydrofolic acid. Also Vitamin A and derivatives thereof are suitable such as retinoic acid and retinaldehyde. Additional examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

The composition of the present invention may contain vitamins and/or coenzymes in an amount of from about 0.001 to about 10% by weight, such as from about 0.01 to about 8% by weight, such as from about 0.05 to about 5% by weight, all weights based on the total weight of the composition.

Alpha or Beta Hydroxy Acids, Alpha Keto Acids

It may also be desired to add one or more alpha or beta hydroxy acids or alpha ketoacids to the compositions of the invention. Suitable alpha hydroxy acids may exist in the keto acid form, or the ester form. Examples of such alpha hydroxy acids include, but are not limited to, glycolic acid, malic acid, pyruvic acid, mandelic acid, lactic acid, methyllactic acid.

Also beta hydroxy acids such as salicylic acid, and derivatives thereof may be included in the compositions of the invention.

The composition of the present invention may contain alpha or beta hydroxy acids, or alpha keto acids in an amount of from about 0.01 to about 20% by weight, such as from about 0.1 to about 15% by weight, such as from about 0.5 to about 10% by weight, all weights based on the total weight of the composition.

The present invention is further described in terms of the following non-limiting examples. Unless otherwise indicated, all parts and percentages are on a weight-by-weight percentage basis.

EXAMPLES

Protocols:
Culture:
Primary Human Dermal Fibroblasts
Light Source:
Hydrosun 500H IRA device (Hydrosun Medizintechnik GmbH, Müllheim, Germany). The IRA device was water-filtered and equipped with a black filter and emits wavelengths between 760 and 1400 nm leading to an irradiance of 360 mW/cm$^2$.

Treatment
Baicalin: stock 44.8 mM in DMSO, and diluted to 10 µM, 25 µM
Phloretin: stock 50 mM in DMSO, and diluted to 1 µM, 5 µM, and 10 µM as final treatment conditions.
Neohesperidin dihydrochalcone: stock 710 mM in DMSO, and diluted to 100 µM, 500 µM, and 1 mM as final treatment conditions.

Cells were incubated with indicated concentration of antioxidant for 24 hrs; followed by a dose of 360 J/cm$^2$ Infrared A radiation, which previously was found to be optimal to induce gene expression without affecting viability in this cell type. Cells were incubated for 24 hrs after irradiation, and then harvested to have MMP-1 mRNA analyzed.

Results:
All treatment was not toxic at doses used.
Baicalin, Phloretin, and Neohesperidin, reduced IRA induced MMP-1 in vitro.

| Compound | Effects in IRA treated cells |
| --- | --- |
| Baicalin | 26% inhibition with 10 µM |
| | 100% inhibition with 25 µM+ (0.001%) |
| Phloretin | 22% inhibition with 1 µM+ (0.00002%) |
| | 78% inhibition with 5 µM+ (0.00014%) |
| | 68% inhibition with 10 µM+ (0.0028%) |

-continued

| Compound | Effects in IRA treated cells |
| --- | --- |
| Neohesperidin dihydrochalcone | 100% inhibition with 100 µM+ (0.006%) |
| | 100% inhibition with 500 µM+ (0.03%) |
| | 100% inhibition with 1 mM+ (0.06%) |

+significant effect to IRA only treated cells, Kruskal-Wallis one way analysis of variance on ranks

What is claimed is:

1. A method of inhibiting premature aging of human skin caused by exposure to infrared radiation comprising contacting the skin with a composition containing a therapeutically-effective amount of neohesperidin dihydrochalcone and, optionally, bicalin.

2. The method of claim 1 wherein baicalin is employed in a therapeutically-effective amount of from about 0.001 to about 10% by weight, based on the total weight of the composition.

3. The method of claim 1 wherein baicalin is employed in a therapeutically-effective amount of from about 0.01 to about 5% by weight, based on the total weight of the composition.

4. The method of claim 1 wherein baicalin is employed in a therapeutically-effective amount of from about 0.1 to about 1% by weight, based on the total weight of the composition.

5. The method of claim 1 wherein neohesperidin dihydrochalcone is employed in a therapeutically-effective amount of from about 0.001 to about 10% by weight, based on the total weight of the composition.

6. The method of claim 1 wherein neohesperidin dihydrochalcone is employed in a therapeutically-effective amount of from about 0.01 to about 10% by weight, based on the total weight of the composition.

7. The method of claim 1 wherein neohesperidin dihydrochalcone is employed in a therapeutically-effective amount of from about 0.1 to about 5% by weight, based on the total weight of the composition.

8. The method of claim 1 wherein the composition further contains ascorbic acid.

9. The method of claim 8 wherein the ascorbic acid is present in an amount of from about 0.001 to about 25% by weight, based on the total weight of the composition.

10. The method of claim 8 wherein the ascorbic acid is present in an amount of from about 0.01 to about 20% by weight, based on the total weight of the composition.

11. The method of claim 8 wherein the ascorbic acid is present in an amount of from about 0.05 to about 20% by weight, based on the total weight of the composition.

12. The method of claim 1 wherein the composition further contains ferulic acid.

13. The method of claim 12 wherein the ferulic acid is present in an amount of from about 0.00004 to about 20% by weight, based on the total weight of the composition.

14. The method of claim 12 wherein the ferulic acid is present in an amount of from about 0.0004 to about 20% by weight, based on the total weight of the composition.

15. The method of claim 12 wherein the ferulic acid is present in an amount of from about 0.004 to about 20% by weight, based on the total weight of the composition.

16. The method of claim 1 wherein the composition further contains phloretin.

17. The method of claim 16 wherein the phloretin is employed in an amount of from about 0.001 to about 5% by weight, based on the total weight of the composition.

* * * * *

UNITED STATES PATENT AND TRADEMARK OFFICE
CERTIFICATE OF CORRECTION

PATENT NO. : 8,765,693 B2  Page 1 of 1
APPLICATION NO. : 13/584117
DATED : July 1, 2014
INVENTOR(S) : Potin It is certified that error appears in the above-identified patent and that said Letters Patent is hereby corrected as shown below:

In the Claims

Col. 8, line 15, Claim 1: please delete "bicalin" and insert --baicalin--

Signed and Sealed this
Second Day of September, 2014

Michelle K. Lee
*Deputy Director of the United States Patent and Trademark Office*